United States Patent [19]

Harvey et al.

[11] Patent Number: 4,568,281
[45] Date of Patent: Feb. 4, 1986

[54] HEATED DENTAL MIRROR

[76] Inventors: Thomas E. Harvey, 2724 Tulane Dr., Ft. Collins, Colo. 80525; William J. Tobin, P.O. Box 643, Fort Collins, Colo. 80521

[21] Appl. No.: 561,888

[22] Filed: Dec. 15, 1983

Related U.S. Application Data

[63] Continuation-in-part of Ser. No. 266,922, May 26, 1981, abandoned.

[51] Int. Cl.⁴ .......................... A61C 3/00; A61B 1/24
[52] U.S. Cl. ........................................ 433/30; 433/31; 433/32; 219/219
[58] Field of Search ............................ 433/30, 31, 32; 219/219, 505; 128/10, 11, 21, 22; 350/66, 308, 309

[56] References Cited

U.S. PATENT DOCUMENTS

| | | | |
|---|---|---|---|
| 281,224 | 7/1883 | Goodsell et al. | 219/219 |
| 709,812 | 9/1902 | Bennett et al. | 219/219 |
| 1,843,067 | 1/1932 | Maximilian de Terra | 219/219 |
| 1,925,981 | 9/1933 | Hopkins | 433/31 |
| 1,934,110 | 11/1933 | Wilson | 433/31 |
| 2,120,091 | 6/1938 | Densten | 219/219 |
| 3,414,704 | 12/1968 | Flanagan | 219/210 |
| 3,686,473 | 9/1972 | Shirn et al. | 219/219 |
| 3,790,748 | 2/1974 | Van Laethem et al. | 219/219 |
| 3,839,620 | 10/1974 | Seibel et al. | 219/219 |
| 4,060,712 | 11/1977 | Chang | 219/219 |
| 4,071,736 | 1/1978 | Kamerling | 219/219 |
| 4,104,509 | 8/1978 | Van Bokestal et al. | 219/544 |
| 4,237,366 | 12/1980 | Berg | 219/219 |
| 4,292,499 | 9/1981 | Kleinschmidt et al. | 219/308 |

FOREIGN PATENT DOCUMENTS

| | | | |
|---|---|---|---|
| 2341615 | 2/1975 | Fed. Rep. of Germany | 433/32 |
| 2137457 | 12/1972 | France | 219/219 |
| 2042344 | 9/1980 | United Kingdom | 128/21 |

Primary Examiner—John J. Wilson
Attorney, Agent, or Firm—Young & Martin

[57] ABSTRACT

A self-temperature regulating hermetically sealed dental mirror includes a mirror encasement comprised of an inverted metal cup that contains electronic heating and temperature control components secured in its interior cavity by a heat conductive resin base potting material. The external surface of the closed end of the cup is a light reflective surface that functions as a mirror. The open end of the inverted cup is imbedded in a plastic base that is molded around and sealed to the sides of the cup in such a manner that the potting material and electronic components are completely sealed and not exposed to the exterior. A molded handle extends radially outwardly from the base, and electric wire leads for conducting electricity to the heating components are positioned longitudinally through the handle. A male jack plug is molded into the distal end of the handle for connecting the wire leads to a power source. The electronics is low voltage direct current and includes a wire wound resistor heating element with a posistor controlled transistor switching circuit for temperature control. Alternatively, for relatively lower wattage heating requirements, the low voltage circuit includes a posistor or a plurality of posistors in series that function both generate heat and regulate the temperature.

15 Claims, 8 Drawing Figures

HEATED DENTAL MIRROR

BACKGROUND

This patent application is a continuation-in-part of U.S. patent application, Ser. No. 266,922, filed May 26, 1981, now abandoned.

The present invention is related to dental mirrors and more specifically to an electronically-heated dental mirror with internal self-regulating temperature control for preventing formation of condensation on the mirror surface.

Dentists commonly use a small mirror mounted on the end of a handle, sometimes referred to as a stomatoscope, as a tool to see in the patient's mouth when performing dental work in areas of the mouth not visible from the exterior. It is a common experience of dentists as well as physicians and veterinarians who use such mirrors to struggle with the frustration of impaired vision caused by condensation on the mirror surface from the patient's warm, moist breath which makes work in such remote areas of the mouth very difficult.

For many years, people have tried with only limited success to alleviate such frustrating problems caused by condensation by attempting to provide mirror surfaces that resist the formation of condensation. For example, U.S. Pat. No. 281,244, issued to Goodsell, et al, U.S. Pat. No. 709,812, issued to Bennett, et al, U.S. Pat. No. 1,934,110 issued to Wilson, and U.S. Pat. No. 2,120,091, issued to Densten, all disclose various embodiments of dental mirrors having electrical heating elements or coils adapted to heat the mirrors to prevent condensation. While the Goodsell, Bennett and Wilson devices include electrical resistance heating elements positioned behind the mirror surface, the Densten patent discloses a device having a heating coil in the handle of the mirror device rather than behind the reflective surface itself. U.S. Pat. No. 1,843,067, issued to De Terra, discloses a somewhat different approach in which a quantity of liquid glycerine is placed behind the mirror to serve as a heat sink or storage body which is heated by an external gas flame before insertion into the patient's mouth.

There are a number of problems associated with these early heated dental mirror devices which have not heretofore been solved. Temperature control has always been a problem in that the temperature must be maintained high enough to prevent condensation on the mirror but low enough to prevent burning or even unpleasant sensation on a patient's skin. Because of the relatively small size of dental mirrors necessary to fit comfortably in a patient's mouth along with other instruments used by the dentist, temperature control for such devices has not been heretofore resolved in a satisfactory manner by the prior art devices. In fact, none of the prior art heated dental mirrors have any kind of temperature control that is sensitive to the temperature of the mirror or even the environment in the vicinity of the mirror.

Another problem is safety associated with the construction and durability of the dental mirror. Since the device is used primarily inside a patient's mouth, it must be safe with virtually no possibility of debilitating or painful electric shock, and the mirrors must also be constructed in such a way as to protect the heating and control components from the moist environment inside the patient's mouth as well as in conventional dental sterilization processes such as phenol or alcoholic liquid sterilizers and autoclave or heat and pressure type sterilization devices. The prior art dental mirrors provide no protection from burns, the electric power requirements were dangerous, and structural integrity was inadequate to provide uncompromised comfort and safety for the patient. Consequently, electrically heated dental mirrors have been largely abandoned by the dental profession. Anti-condensation dips, such as liquid silicone solutions are probably the most widely used method at the present time for preventing condensation on dental mirrors, although a more esoteric turbo-centrifugal dental mirror has also been developed recently in which the reflective surface portion of the mirror is kept spinning constantly by an air turbine to physically remove condensation and droplets of water by centrifugal force. These methods also have problems. For example, the dip solutions are effective only as long as they are on the surface of the mirror, but they are washed off the mirror whenever the dentist cleans his mirror of debris with a stream of water, and the tubrocentrifugal mirror is too large, only partially effective, and is vulnerable to invasion of debris, moisture, and liquid sterilization fluids in ordinarily inaccessible portions of the machinery.

SUMMARY OF THE INVENTION

Accordingly, it is also an object of the present invention to provide a novel and improved electronically-heated dental mirror structure that is efficient in heating the mirror surface with good temperature recovery characteristics when the mirror surface is cleaned and in which the electronic heating and control components are hermetically sealed in the mirror adjacent the light reflective surface of the mirror in such a manner that they are isolated from moisture and impervious to and unaffected by conventional dental steriliation techniques.

It is also an object of the present invention to provide a new and improved heated dental mirror in which the temperature of the mirror surface can be heated to and maintained at a temperature range high enough to prevent condensation on the mirror surface yet low enough to not be uncomfortable to a patient if the mirror touches the surface of the inside of the patient's mouth.

It is also an object of the present invention to provide an electronically-heated dental mirror with internal automatic temperature control sensitive to the mirror temperature while in the patient's mouth to maintain the temperature of the mirror at or near the range of normal body temperature to prevent condensation thereon.

It is also an object of the present invention to provide well proportioned and appropriately sized electronically-heated dental mirror that is safe for patients from the standpoint of preventing both electric shock and excessive heat, comfortable for the dentist to use, and inexpensive to manufacture.

The heated dental mirror of the present invention is comprised of a wafer-shaped heated mirror element mounted and hermetically sealed in a plastic base with a handle extending outwardly therefrom. The mirror element is comprised of an inverted cup or case with the electronic heating and temperature control components positioned and retained solidly therein by a potting material. The cup is preferably metallic or other material of high heat conductivity and the potting material preferably has a moderate to high specific heat characteristic or thermal capacity and low to moderate heat conductivity to function as a heat sink to enhance temperature recovery at the mirror surface when the mirror surface is cooled momentarily, such as by flushing with a stream of water, air, or the like. The external surface of the inverted cup has a shiny, light reflective surface thereon to function as a mirror. The wafer-shaped mirror element or encasement is imbedded in an inverted position in a plastic support base that completely encloses the potting material and open end of the inverted cup and returns upwardly along the sides of the inverted cup to hermetically seal the electronic heating and control components inside the mirror encasement from the external environment. A handle portion extends radially outwardly from the vase with the electric leads for powering the heating components embedded longitudinally in the handle. The distal end of the handle terminates in a jack plug connector to which the electric leads in the handle are connected and which is molded into the plastic handle in a manner such that the electric wires and internal connections of the jack plug are also hermetically sealled from the exterior environment.

Several alternative heating and electronic control circuits are provided. In one embodiment, a heat sensitive posistor and transistor-controlled wire wound resistor are provided. In other embodiments, posistors are used to both produce the heat and to control the temperature. The posistors are doped to increase dramtically in resistivity at a preferable temperature range for safe, comfortable use in a patient's mouth while eliminating condensation on the mirror surface, i.e. about 32° C. to 37° C. (89° F. to 99° F.).

BRIEF DESCRIPTION OF THE DRAWINGS

Other objects, advantages and capabilities of the present invention will become more apparent as the description of the preferred embodiments is continued, as considered in conjunction with the drawings in which.

DESCRIPTION OF THE PREFERRED EMBODIMENTS

Figure 1:
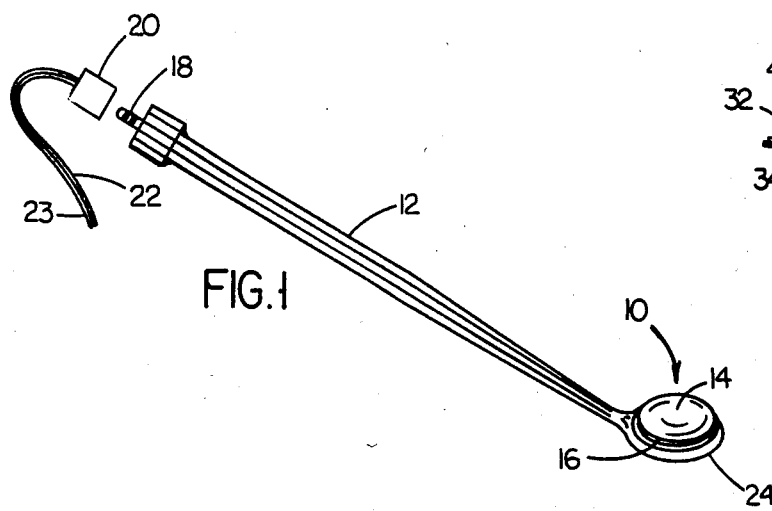
FIG. 1 is a perspective ciew of the heated dental mirror of the present invention.

The heated dental mirror 10 of the present invention, as shown in FIG. 1, is generally of a conventional shape and size for dental mirrors It includes a light reflective surface 14, which functions as a mirror, supported by an enlarged, rounded base 24. An elongated handle 12 extends radially outwardly and slightly upwardly from the base support 24. A male jack plug 18 is molded in the distal end of the handle 12 and is adapted for electrical connection with a mating female jack plug socket 20 on the end of two wire leads 22, 23 from a power source (not shown).

A unique feature of the dental mirror 10 of the present invention is the structure of the heated mirror portion in which the electronic heating and temperature control components are encapsulated in a wafer-like, generally cylindrical encasement, the external surface of which is a light reflective surface 14 that functions as a mirror. The cylindrical encasement is comprised of a shallow, generally cylindrical metallic cup 16, such as that shown in FIG. 3, which contains the electronic heating and temperature control components. One end of the cup 16 is enclosed and the sides 28 have a slightly concave configuration with the open end flared outwardly.

Figure 3:
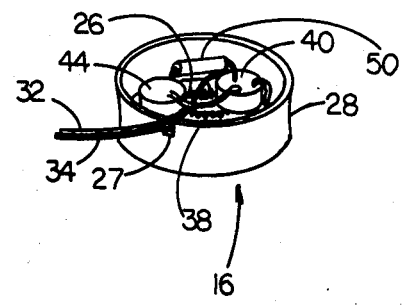
FIG. 3 is a perspective view of the cup-shaped mirror case in which the electronic heating and control components are positioned.

The electronic heating and temperature control components shown in FIGS. 2 and 3 include a wire wound resistor 38, transistor 40, resistor 50, and posistor 44, the functions of which will be described below. These electronic components are positioned in the container or cup 16 with the wire leads 32, 34 extending out of the cup 16 through a notch 27 in the sidewall 28. These electronic components are then encapsulated in the cup 16 by pouring in a liquid resin-based potting material 29 into the cavity of interior of the cup 16 around the electronic components. The potting material 29 is allowed to harden to secure the components in place and to permanently fill all the voids or empty space in the cavity of cup 15 around the electronic components. The potting material 29 is preferably a metarial having a moderate to high specific heat or thermal capacity to function as a heat sink or thermal reservoir but a low to moderate contuctivity so that the heat generated by the electronic heating element is dispersed uniformly throughout the wafer-like mirror encasement but is not readily lost by conduction for advantages to be described below. The cup 16 with the electronic components encapsulated therein is then inverted and molded into the plastic support base 24. The handle with the wire leads 32, 34 embedded longitudinally therein is in a unitary embodiment with the supoort base 24.

Figure 2:
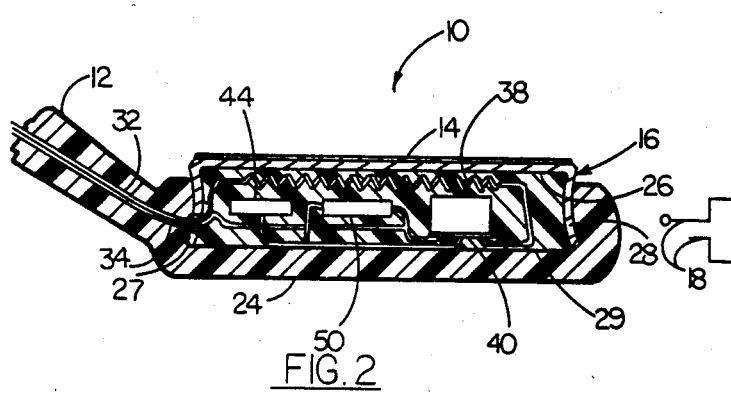
FIG. 2 is a cross-sectional view of one embodiment of the heated dental mirror showing the placement of the heating and temperature control components.

As shown in FIG. 2, the heated mirror encasement is embedded in the plastic support base 24 with the open end of the inverted cup 16 and a portion of the sides 28 completely engulfed by the base 24 to form a hermetic seal to isolate the electronic components and potting material from the exterior environment. The handle 12 is also molded around the wire leads 32, 34 and around the male jack plug 18 in such a manner that the electronic components and wires in the mirror apparatus 10 are hermetically sealed from the exterior, with the exception of the contact prong of the male jack plug 18 which extends longitudinally outwardly from the distal end of the handle 12 as shown in FIG. 1. The concave and slightly flared sidewalls 28 of the inverted cup 16 anchor the cup 16 into the molded plastic support base 24 so that the cup 16 cannot be removed and to maintain the hermetic seal.

As mentioned above briefly, a light reflective surface 14 is provided on the external surface of the enclosed end 26 of the cup 16 to function as a mirror. The light reflective surface 26 is preferably a polished metallic plating, such as chrome, on the metallic cup 16 both of which have a high heat conductivity to conduct heat readily from the interior of the encasement to the surface to prevent condensation thereon. The metallic reflective surface 14 can also be deposited by other state of the art means such as sputtering and the like.

Figure 4:
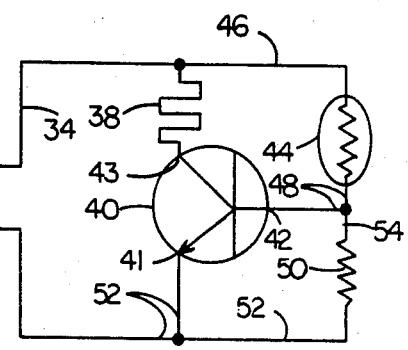
FIG. 4 is the electronic circuit diagram for the embodiment shown in FIG. 2.

As shown in FIGS. 2 and 4, the electronic heating and temperature control components of one of the preferred embodiments includes a wire wound resistor 38 for generating heat, a transistor 40 for regulating the electric power to the wire wound resistor 38, a posistor 44 for controlling the transistor 40, and a balance resistor 50 for balancing the circuit and biasing the transistor 40 appropriately. This circuit is basically a DC operated circuit wherein electricity is supplied through leads 32 to the emitter 41 of the transistor 40. The wire wound resistor 38 is connected to the collector 43 of the transistor 40, and the electric lead 34 is connected from the wire wound resistor 38 back to the opposite terminal of the jack plug 18. The posistor 44 is preferably a semiconductor device that has a positive temperature coefficient of resistance that remains relatively constant at lower temperatures (the cold temperature range) to a critical of "knee" temperature of approximately 35° C. (95° F.), where the positive temperature coefficient of resistance increases dramatically to have the practical effect of stopping electric current through the posistor. In this manner, with the posistor 44 connected on one side to the base 42 of the transistor 40 by lead 48 and on the other side to lead 34 by lead 46, at lower temperatures or in the cold temperature range electricity is conducted through the posistor 44 relatively easily at its normal cold temperature ohm value, thereby allowing a large electric current draw through wire wound resistor 38 to generate heat. When the temperature in the mirror encasement reaches "knee" at approximately 35° C., the resistance of the posistor 44 increases dramatically and virtually cuts off electric conduction through the posistor, which in turn causes the transistor to shut off the electric current draw through the wire wound resistor 38. With the electric power shut off to the wire wound resistor 38, it no longer generates heat and the temperature of the mirror encasement does not rise above the selected critical 35° C. As the temperature falls below the critical temperature of 35° C., the posistor 44 again conducts electricity, thereby signaling the transistor 40 to again power the wire wound resistor 38 to generate heat. The balance resistor 50, which is provided to balance the circuit and bias the transistor, is connected to lead 32 by lead 52 and to lead 48 by lead 54.

Figure 5:
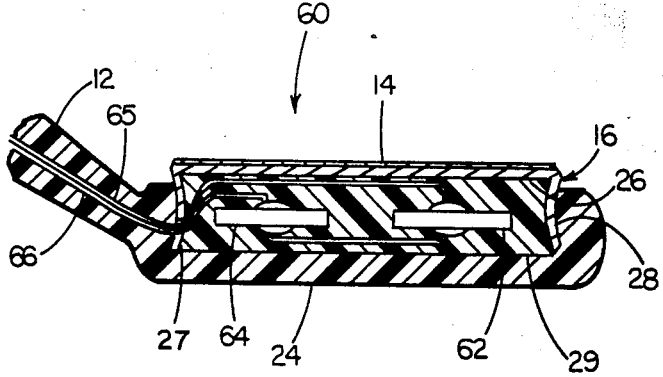
FIG. 5 is a cross-sectional view of an alternative embodiment with two posistor heating and temperature control elements.
Figure 7:
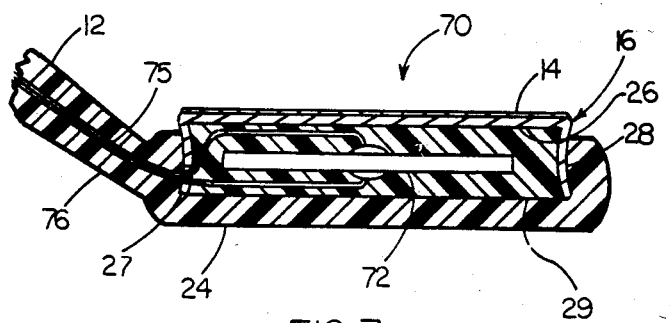
FIG. 7 is a cross-sectional view of the heated dental mirror of the present invention with an embodiment having one posistor heating and temperature control element.

Several alternative electronic heating and temperature control circuits can also be used advantageously, particularly where power requirements for sufficient heating are relatively low. For example, in the heated dental mirror embodiments 60 and 70 shown in FIGS. 5 and 7, respectively, the posistors have sufficient resistivity in the cold temperature range that they are capable of generating sufficient heat themselves to heat the mirror encasement as well as to automatically maintain the temperature of the light reflective surface 14 at approximately the desired temperaure of 35° C. (95° F.). In other words, when used as taught by this invention, the posistor material acts as both the heat generator to heat the reflective surface 14 and also as its own temperature regulator to maintain the temperature at or near the desired 35° C., temperature range. In the cold state, i.e., below 35° C., the resistivity of the posistor is relatively low and a large current is drawn. Therefore, in the cold state, relatively high power and heat are dissipated. As the mirror encasement heats up due to the thermal dissipation from the posistor, and as the temperature reaches approximately 35° C., the posistors are doped with materials to cause an abrupt and drastic increase in resistance, thereby significantly decreasing the current draw. With the lower current draw, the heat dissipated is likewise decreased such that a balance is maintained at the desired 35° C. temperature range. As shown in FIGS. 5 and 7, the structures of these two alternative embodiments, 60, 70, respectively of the heated dental mirror are similar to that of the embodiment shown in FIG. 2 and described above. The electrical heating and temperature control components, i.e., the posistors, are encapsulated in an inverted cup or case 16 with a solidified resin base potting material 29. As described above, the cup or case 28 is inverted and imbedded in a molded plastic support base 24 which hermetically seals the open end of the case 28 and electric components while leaving the light reflective surface 14 on the exterior of the end cap 26 exposed to function as a mirror.

Figure 6:
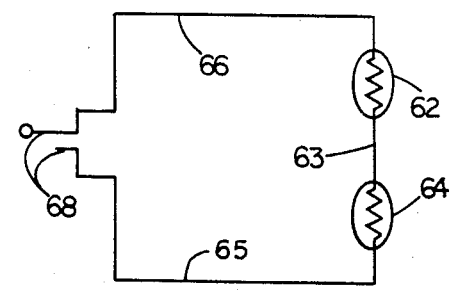
FIG. 6 is an electronic circuit diagram of the embodiment shown in FIG. 5.

In practical use, it has been found that approximately 0.35 watts are sufficient to heat the encapsulated mirror encasement to approximately 35° C. in about two minutes. A power draw of about 0.35 watts is also effective to maintain the temperature in the range where condensation will not form or remain on the light reflective surface 14 during normal usage where the mirror is only in contact with air and conductivity of heat away from the mirror is not excessive. Therefore, in an application such as that shown in FIGS. 5 and 6, a 24-volt power source can be used, and two posistors 62, 64 are connected in series by lead 63 to provide sufficient resistance to draw approximately 0.35 watts. In this kind of circuit, each posistor has a resistance of approximately 825 ohms. Both posistors 62, 64 connected in series provide the required 1,650 ohms to draw approximately 15 milliamps at 24 volts to produce the required 0.35 watts of power. The leads 65, 66 connect the posistors 62, 64 to the jack plug 68.

Figure 8:
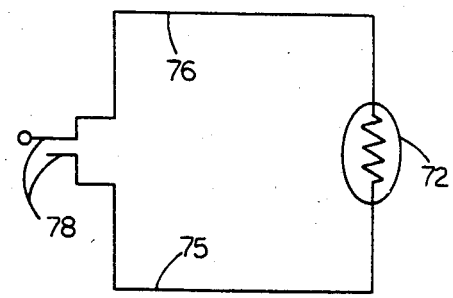
FIG. 8 is an electronic circuit diagram for the embodiment shown in FIG. 7.

While 24 volts, as required by the embodiment in FIG. 5, is perfectly safe for use in a person's mouth, it is close to the threshold of a person's senses for feeling in electric shock. Therefore, in the extremely unlikely event there could be some kind of short circuit in the heated dental mirror while in the patient's mouth, the electricity could possibly be felt by the patient. Therefore, it is preferable to use an even lower voltage, which would not only be safe but also below the threshold of sensation for most persons. A potential of 18 volts in the range of 20 milliamps is below the threshold sensation of an average person, and 120/18-volt transformers are commercially available. Also, posistors with a resistance characteristic of approximately 1,250 ohms in the cold temperature range required to produce approximately 0.35 watts at 18 volts with a 20 milliamp current draw are also commercially available. Therefore, the embodiment 70 shown in FIG. 7, with the electronic circuit shown in FIG. 8, has one larger posistor 72 with a resistance of approximately 1,250 ohms in the cold temperature range. This embodiment is a very practical, simple, inexpensive and easily manufactured electronic heating and temperature control circuit for a dental mirror in accordance with this invention which is safe for use in a patient's mouth. As shown in FIGS. 7 and 8, electric leads 75, 76 connect the single posistor 72 to the terminals of the jack plug 78.

As discussed above, it has been found that a power output of approximately 0.35 watts is a practical heating criterion for a dental mirror for heating the light reflective surface 14 to a temperature range of between 32° C. and 37° C. (89° F. and 99° F.) and preferably approximately 35° C. (95° F.), which is a temperature several degrees below normal body temperature, at which condensation from a person's breath will not occur on the mirror surface. The mirror at this desired temperature will not feel hot nor uncomfortable if it comes in contact with the skin tissue on the inside of a person's mouth. In this temperature range, the mirror merely feels comfortably warm while preventing condensation on the light reflective surface making it significantly easier and less frustrating for a dentist to maintain good clear vision of the area in the patient's mouth in which he is working.

As mentioned above briefly, the light reflective surface 14 on the exterior of the mirror encasement is preferably a polished chrome plating on an inverted brass cup 16. The brass cup 16 and metallic chrome light reflective surface 14 have high thermal conductivity characteristics and conduct heat quickly from the interface of the brass cup 16 with the heat sink potting material 29 in the interior of the encapsulated encasement to the exterior surface to maintain the temperature at the light reflective surface at or near the desired temperature of 35° C. Also, as mentioned above, the potting material 29 advantageously has a high specific heat or thermal capacity to store heat, but it has a low thermal conductivity so it will also retain a significant amount of heat without giving it up easily to surrounding materials or environment. This feature is advantageous for prompt temperature recovery on the light reflective surface when heat has been lost therefrom by contact with other materials or abnormal environment, even where the power draw is only in the low range of 0.35 watts as preferred in this invention.

For example, when drill debris or saliva from the patient's mouth is deposited on the light reflective surface 14, and the dentist finds it necessary to clean the light reflective surface, he can flush the surface by directing a stream of water or compressed air onto the surface, which probably would have the effect of conducting abnormal amounts of heat away from the exterior surface of the mirror and would decrease the temperature of the light reflective surface 14 significantly. However, since the potting material heat sink 29 is low in thermal conductivity, the heat retained therein is not lost immediately to the flush water or stream of compressed air. Usually, such flushing or cleaning is accomplished in a few seconds, so when it is completed, the high thermal conductive metallic cup 16 immediately draws sufficient heat from the heat sink 29 for the light reflective surface 14 to quickly recover the desired temperature range of approximately 35° C. to prevent condensation thereon. Clear vision is maintained, and the dentist loses little or no time in continuing his work. Of course, prolonged exposure to a stream of compressed air or water would ultimately draw down the heat available in the heat sink and lower the temperature thereof to the point where several minutes might be required for the mirror encasement to recover the desired temperature; however, in practice such prolonged exposure to a stream of water or compressed air is not normally encountered.

The potting material 29 should also be an electrical insulator so that it does not interfer with the electronic components embedded therein. Since sterilizing techniques in dental offices often involve the use of chemical solution or pressurized, high temperature autoclaves, this potting material 29 should also be resistant to chemical degradation by solvents, acids, and alkalis, as well as being resistant to pressure and temperature to maintain its structural integrity. Finally, it is preferable that this material be conducive to use with conventional manufacturing techniques and equipment. It is probably not possible to provide a material that exhibits the highest level of all these qualities together. Even so, it has been found that, as an example, a nucleated homopolymer manufactured by Shell Chemical Company, known as Shell Polypropylene 5824S, has a good balance of these characteristics that make it suitable for use in this invention. This material has a thermal conductivity of 0.81 BTU in/hr ft$^2$ °F. and a specific heat of 0.46 BTU/lb °F. Also, its volume resistivity is $1.0 \times 10^{17}$ ohm cm$^3$, and its Vicat softening temperature is 305° F.

Although the present invention has been described with a certain degree of particularity, it is understood that the present disclosure has been made for clarity and example and that changes in details of structure may be changed without departing from the spirit thereof.

We claim:

1. Heatable dental mirror apparatus, comprising in combination:
   a hot plate in the form of a mirrored inverted cup-shaped container having a light reflective impermeable external surface adapted for use as a mirror and self temperature regulated electronic heating means positioned in said cup-shaped container for heating said reflective surface and maintaining the temperature of said reflective surface in the range of 32° C. to 37° C., said electronic heating means being set in a heat sink potting material that has a moderate to high specific heat and moderate to low thermal conductivity that fills the cavity in said container around said electronic heating means and which is hardened to hold said electronic heating means in immovable position in said container; and
   handle means for supporting said mirrored hot plate, the open side of said container and said electronic heating means being hermetically sealed by said handle means, and said reflective surface being exposed for use as a mirror.

2. The heatable dental mirror apparatus of claim 1, wherein said assembly of electronic components and potting material in said container is a heat sink having high specific heat and low thermal conductivity, wherein the thermal conductivity of said container is greater than the thermal conductivity of said heat sink.

3. The heatable dental mirror apparatus of claim 2, including electrical wire leads for conducting electrical power to said electronic heating means from an external electric power source, said wire leads being connected to said electronic heating means in said container and extending through said handle means to the distal end thereof, and a male dual contact jack plug terminal mounted in said distal end of said handle means in such a manner that said handle means hermetically seals all electrical connections, leads, heating and temperature control components except the male plug contact portion of said jack plug.

4. The heatable dental mirror apparatus of claim 2, wherein said container is a metallic cup, and said light reflective surface is a polished reflective metallic plate coating on the external surface of said container.

5. The heatable dental mirror apparatus of claim 2, wherein said electronic heating means is temperature controlled by a current regulating posistor material positioned adjacent said reflective surface and having a relatively constant electronic resistivity in cold temperature ranges from about 15° C. to about 35° C. and a sharply increased resistivity about 35° C.

6. The heatable dental mirror apparatus of claim 5, wherein said electronic heating means is driven by a low voltage power source having a voltage below a person's threshold of sensation and a posistor material having sufficient resistivity and heat generating characteristic at such low level voltage of heat said light reflective surface from room temperature to about 35° C. in a time range of one to three minutes.

7. The heatable dental mirror apparatus of claim 5, wherein said electronic heating means is driven by a low voltage power source having a voltage below a person's threshold of sensation and a transistor controlled resistance heating element, said transistor being current regulated by said posistor to shut down said heating element when the temperature reaches about 35° C. and to operate said heating element when the temperature falls below about 35° C.

8. Self-temperature regulating heated dental mirror apparatus, comprising a thin-walled member having a light reflective mirror surface, and a high thermal conductivity, and an electronic semi-conductor heat generating material having a positive temperature coefficient of resistance that increases sharply in a knee temperature range of about 89° F. to 99° F. (31.7° C. to 37.2° C.) positioned adjacent said reflective surface, both said reflective surface and said semi-conductive material being mounted in a body adapted for insertion into a dental patient's mouth and having a handle portion extending outwardly therefrom, said electronic semiconductor heat generating material having a resistance in the cold temperature range below and up to said knee temperature range of about 1,000 to 1,700 ohms and is driven by approximately 15 to 25 volts to draw approximately 0.25 to 0.45 watts of power for heat generation, wherein the resistivity of said semiconductor heat generating material changes at said knee temperature range such that its resistance in temperature ranges above said knee temperature range is too high to draw sufficient power when driven by approximately 15 to 25 volts to generate heat at a rate necessary to balance the thermal loss from the mirror apparatus to the environment surrounding the mirror, thereby resulting in the inability of said semicondcutor heat generating material to heat the mirror apparatus above said knee temperature range, said light reflective surface being positioned adjacent said heat generating material with a mass of heat sink material engulfing said heat generating material and being in contact with said mirror member over substantially its entire surface opposite said light reflective surface, said mass of heat sink material having a high specific heat and low thermal conductivity, the thermal conductivity of said mirror member being higher than the thermal conductivity of said heat sink material.

9. The method of heating a dental mirror, comprising the steps of:
providing a light reflective surface on the exterior surface of a thin-walled container having a high thermal conductivity;
placing an electronic heat generating component in the interior of said thin-walled container opposite said reflective surface;
filling the space in the interior of the container engulfing said electronic heat generating component with a heat sink material having a high specific heat and a low thermal conductivity in such a manner that substantially all of said interior surface of said thin-walled member is in contact with said heat sink material; and
connecting said electronic heat generating component to an electric power source.

10. The method of heating and controlling the temperature of a dental mirror, comprising the steps of:
positioning an electronic generating material having a positive temperature coefficient of resistance that increases sharply at a temperature range high enough to prevent condensation from a person's breath and low enough to be comfortable to a person's skin on contact therewith adjacent a surface of a thin-walled metallic member having a light reflective surface thereon opposite the surface adjacent said heat generating material and having a high thermal conductivity;
engulfing said heat generating material in a heat sink material having a high specific heat and a lower thermal conductivity than said thin-walled metallic member in such a manner that said heat sink material is in contact with said surface of said thin-walled member opposite said light reflective surface; and
driving said material to produce heat by connecting the material to a source of electric power sufficient to heat said material and the adjacent mirror surface to said temperature range.

11. The method of claim 10, including the step of driving said material to draw about 0.25 to 0.45 watt of power.

12. The method of claim 11, including the steps of providing said material to have a resistance of about 1,000 to 1,700 ohms at temperatures below said temperature range, and driving said material with about 15 to 25 volts.

13. The method of claim 10, including the steps of providing said material to have resistance low enough below said temperature range to draw sufficient current to heat said adjacent mirror surface to said temperature range and to have resistance high enough above said temperature range to draw insufficient current above said temperature range to heat said adjacent mirror surface above said temperature range.

14. The method of claim 10, including the step of disbursing the heat generated by said material to said adjacent mirror surface by encapsulating said material in a potting substance in such a manner that both said material and the rear side of said mirror surface are in contact with said potting substance.

15. The method of claim 10, including the step of positioning additional resistor heating means adjacent the mirror surface and adjacent said electronic heat generating material, and regulating the electric current flow through said resistor with transistor means and controlling said transistor means with said electronic heat generating material.

* * * * *